United States Patent [19]

Fosslien

[11] 4,106,155

[45] Aug. 15, 1978

[54] APPARATUS FOR WASHING CONTAMINATED LABORATORY CONTAINERS

[75] Inventor: Egil Fosslien, Tampa, Fla.

[73] Assignee: Cortex Research Corporation, Tampa, Fla.

[21] Appl. No.: 729,962

[22] Filed: Oct. 6, 1976

[51] Int. Cl.² ........................... A74L 7/00; B08B 9/08
[52] U.S. Cl. ....................................... 15/321; 15/304; 134/99; 134/156; 134/171
[58] Field of Search ................. 15/302, 304, 320, 321, 15/322; 134/94, 99, 156, 169, 171; 141/91, 92

[56] References Cited

U.S. PATENT DOCUMENTS

| | | | |
|---|---|---|---|
| 2,531,370 | 11/1950 | Thompson | 15/321 |
| 2,607,067 | 8/1952 | Minerley | 15/353 X |
| 2,814,575 | 11/1957 | Lange, Jr. | 134/171 X |
| 3,355,762 | 12/1967 | Cavell et al. | 15/321 |
| 3,639,939 | 2/1972 | Crener et al. | 15/320 |
| 3,849,830 | 11/1974 | Wagner | 134/171 X |
| 3,916,924 | 11/1975 | McGowan | 134/171 X |
| 3,949,771 | 4/1976 | Dodge et al. | 134/94 |

Primary Examiner—Christopher K. Moore
Attorney, Agent, or Firm—Koenig, Senniger, Powers and Leavitt

[57] ABSTRACT

Apparatus for washing contaminated laboratory containers such as test tubes, flasks and the like. A tube, one end of which is connected to a source of negative pressure and the other end of which is inserted into a contaminated container, has a length sufficient to reach the bottom of the container to remove by aspiration material therein. A pump is connected to a source of washing material and, when actuated, delivers washing material into the container. Actuation of the pump interrupts aspiration during delivery of washing material. The washing material thus delivered to the container and contaminants are withdrawn by aspiration from the container after the pump is deactuated.

18 Claims, 5 Drawing Figures

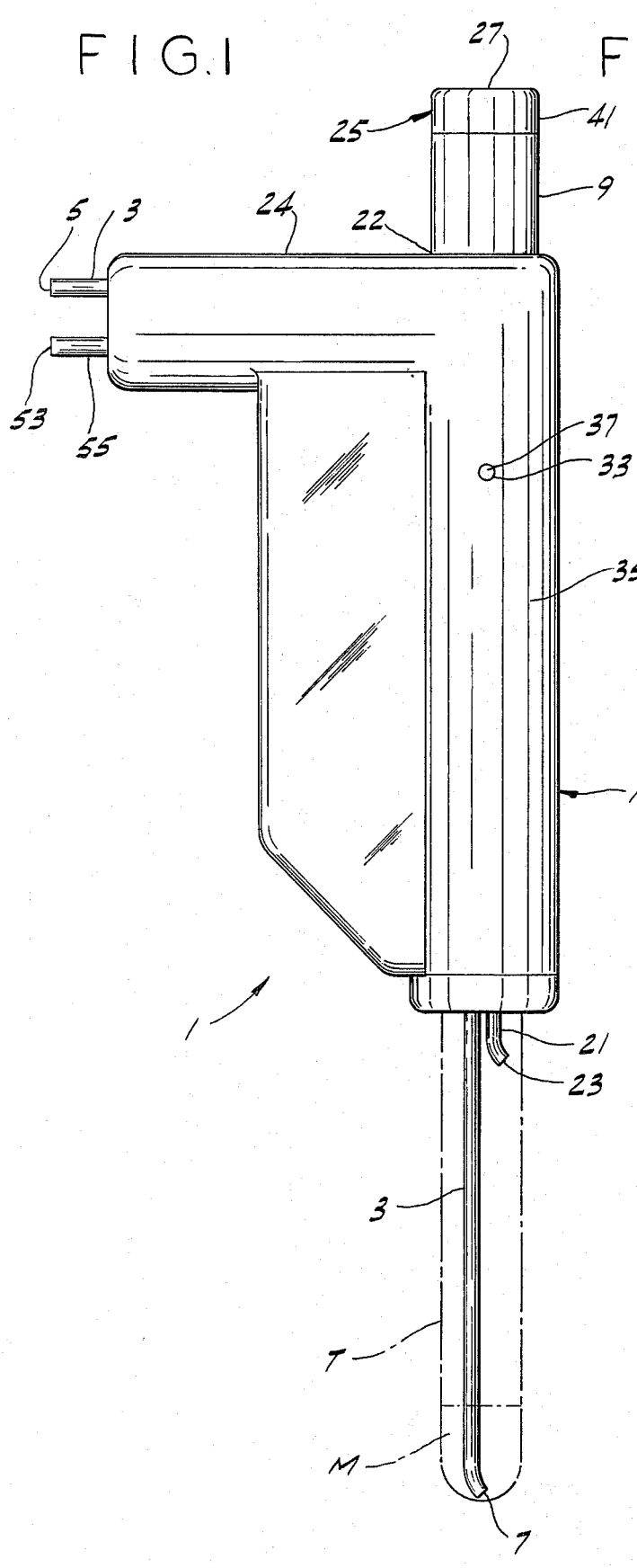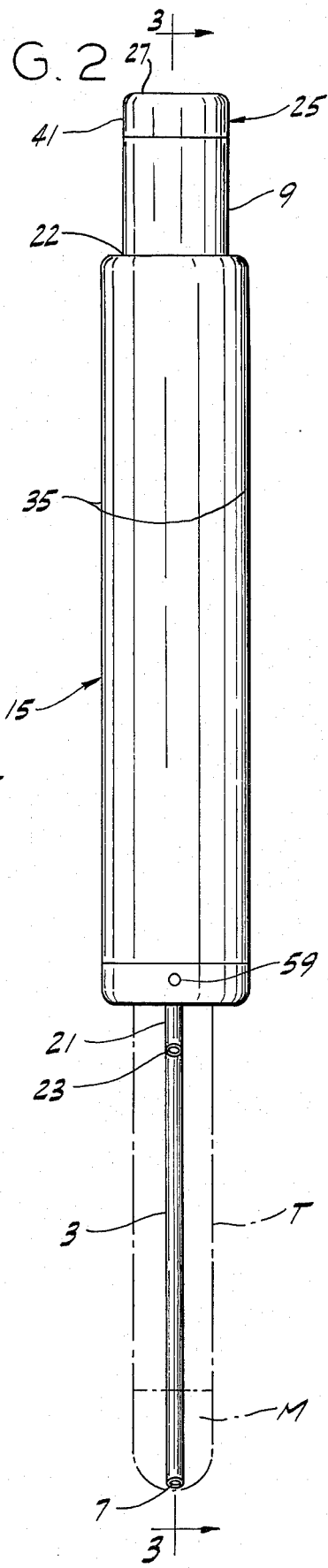

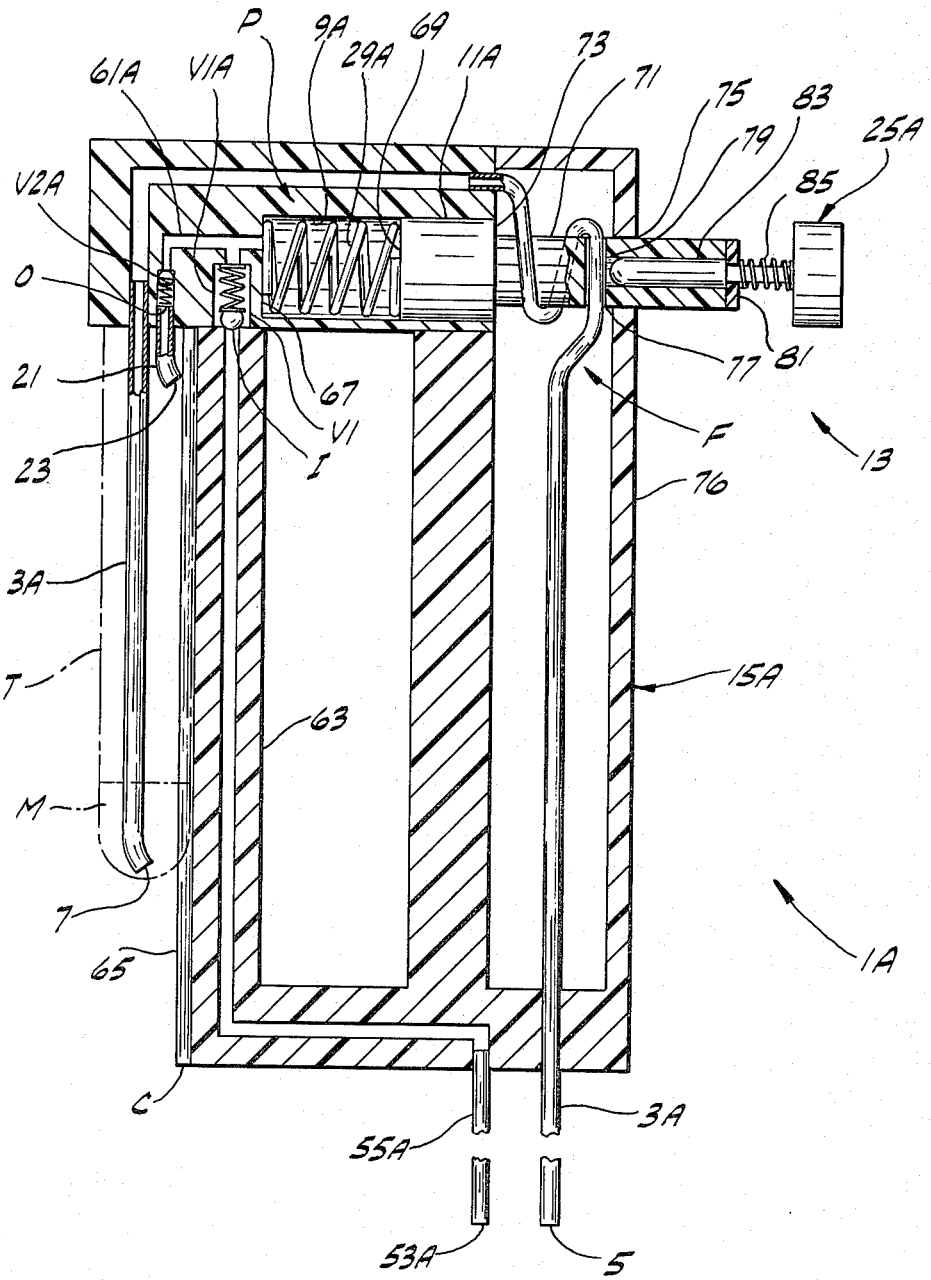

APPARATUS FOR WASHING CONTAMINATED LABORATORY CONTAINERS

BACKGROUND OF THE INVENTION

This invention relates to laboratory equipment and more particularly to apparatus for washing and cleaning contaminated test tubes, flasks and the like used in laboratory work.

In radioimmunoassay testing, for example, one problem encountered is safe disposal of radioactive (contaminant) material after separation of free and bound antibodies or antigens. Radioimmunoassays are in vitro laboratory test procedures increasingly used to determine small amounts of molecules, e.g. antigens, antibodies, hormones, or drugs, because radioimmunoassay testing combines the sensitivity of radioactivity counting with the specificity of antigen-antibody binding.

During such tests, there should be a consistent and complete washing of solid phase radioimmunoassay tubes after incubation and before counting. A radioimmunoassay for hepatitis associated antigen (HAA) serves as an example. Reagent tubes for this test would contain an inside, bottom sandwiched layer consisting of an antibody attached to the inside of the tube and radioactive (labeled) antigen attached to the antibody. Patient serum is precisely diluted in a buffer and a measured amount of the dilution is introduced into the tube whereupon the tube is incubated at a preset temperature for a specified period of time.

During the incubation, hepatitis antigen in the patient's serum will compete with the labeled antigen for the antibody binding sites and will displace some of the labeled antigens; the more antigen that is present in the serum, the more labeled antigen will be displaced. At the end of the incubation period, liquid in the tube is removed and the inside of the tube is washed to insure complete removal of displaced, "free" labeled antigen. The radioactivity of the tube, i.e., the amount of labeled antigen left in the tube is counted by introducing the entire tube into a radioactivity counter, typically a gamma radiation counter. The more radioactivity there is measured, the less antigen there was present in the patient's serum and vice versa.

To obtain consistent results, it is important that the washing of the tube before counting of the radioactivity be gentle but consistent, i.e., the same volume of wash fluid should be used for each tube; gentle so as not to loose bound, labeled antigen. Consistency is necessary for the following reason:

Typically, the radioimmunoassay is calibrated by using sera with known amounts of antigen instead of patient sample. Several sera containing various amounts of antigen are run in a batch with many patient sera and a calibration curve is established based upon the radioactivity in the tubes where calibrator sera were used. The amount of antigen in the patient sera is determined from the calibration curve. Since the amount of bound antigen in the tubes may to some extent depend upon the amount of washing, or some free, labeled antigen may stick to the inside of the tube if not completely washed before counting, it is necessary to be sure that the washing is consistent.

Typically, containers are presently cleaned by first inverting them so that material in the container, including contaminants, flows out the container mouth and into a waste receptacle. Alternately, a suction probe is introduced into the container and material is drawn off through the probe to the receptacle by aspiration. Next, the inside of the container is cleaned with a wash solution which is discharged into the container from a dispensing mechanism such as a syringe dispenser. The dispenser may be adjusted to discharge a predetermined volume of solution into the container and for this purpose has valves which are operated with one hand while the other hand reintroduces the probe into the container after a discharge of solution into it. Since many washes may be necessary to adequately clean the container, the above process may need to be repeated numerous times. The procedure, as outlined, is both tedious to perform and requires the use of both hands to be done properly.

A test tube washer operable with one hand is disclosed in U.S. Pat. No. 3,849,830 and is a handheld unit having a probe for insertion into a test tube and two ports which the user covers with his thumb to draw wash solution, by aspiration, through the probe for circulation around the inside of the test tube with one of the ports then being uncovered to stop the flow of solution to the probe and draw off the material in the test tube. While such a washer may make a cleaning operation less tedious, it has the disadvantages of potentially bringing the material being aspirated into contact with the user, of not being usable with all sizes and types of laboratory containers, and of not accurately metering the amount of wash solution introduced into a test tube.

SUMMARY OF THE INVENTION

Among the several objects of the present invention may be noted the provision of apparatus for cleaning laboratory containers such as test tubes, flasks and the like and which can be held, operated and controlled with only one hand; the provision of such apparatus which will aspirate material, including contaminants, from a container when the apparatus is first brought into contact with it without the user having to perform any other actions; the provision of such apparatus in which the material being aspirated is kept out of contact with the user; the provision of such apparatus for gently delivering washing material into the container and for interrupting aspiration while the washing material is being delivered; the provision of such apparatus for repetitively delivering metered quantities of washing material into the container; the provision of such apparatus wherein aspiration and delivery of washing material is controlled by a single manually operable means; and the provision of such apparatus which is portable, easy to use, light in weight and low in cost.

Briefly, apparatus of the present invention for washing contaminated laboratory containers such as test tubes, flasks and the like comprises a tube, one end of which is connected to a source of negative pressure and the other end of which is inserted into a contaminated container, having a length sufficient to reach the bottom of a container thereby to remove by aspiration material therein. A pump is connected to a source of washing material and, when actuated, delivers washing material into the container. Means responsive to actuation of the pump interrupts aspiration during delivery of washing material and the washing material thus delivered to the container and contaminants are withdrawn by aspiration from the container after the pump is deactuated. Other objects and features will be in part apparent and in part pointed out hereinafter.

BRIEF DESCRIPTION OF THE DRAWINGS

FIG. 1 is a side elevation of apparatus for the present invention for cleaning contaminated laboratory containers;

FIG. 2 is a front elevation of the cleaning apparatus shown in FIG. 1;

FIG. 4 is a sectional view of a second embodiment of cleaning apparatus of the present invention;

Corresponding reference characters indicate corresponding parts throughout the several views of the drawings.

DESCRIPTION OF PREFERRED EMBODIMENTS

Figures 3, 3A:
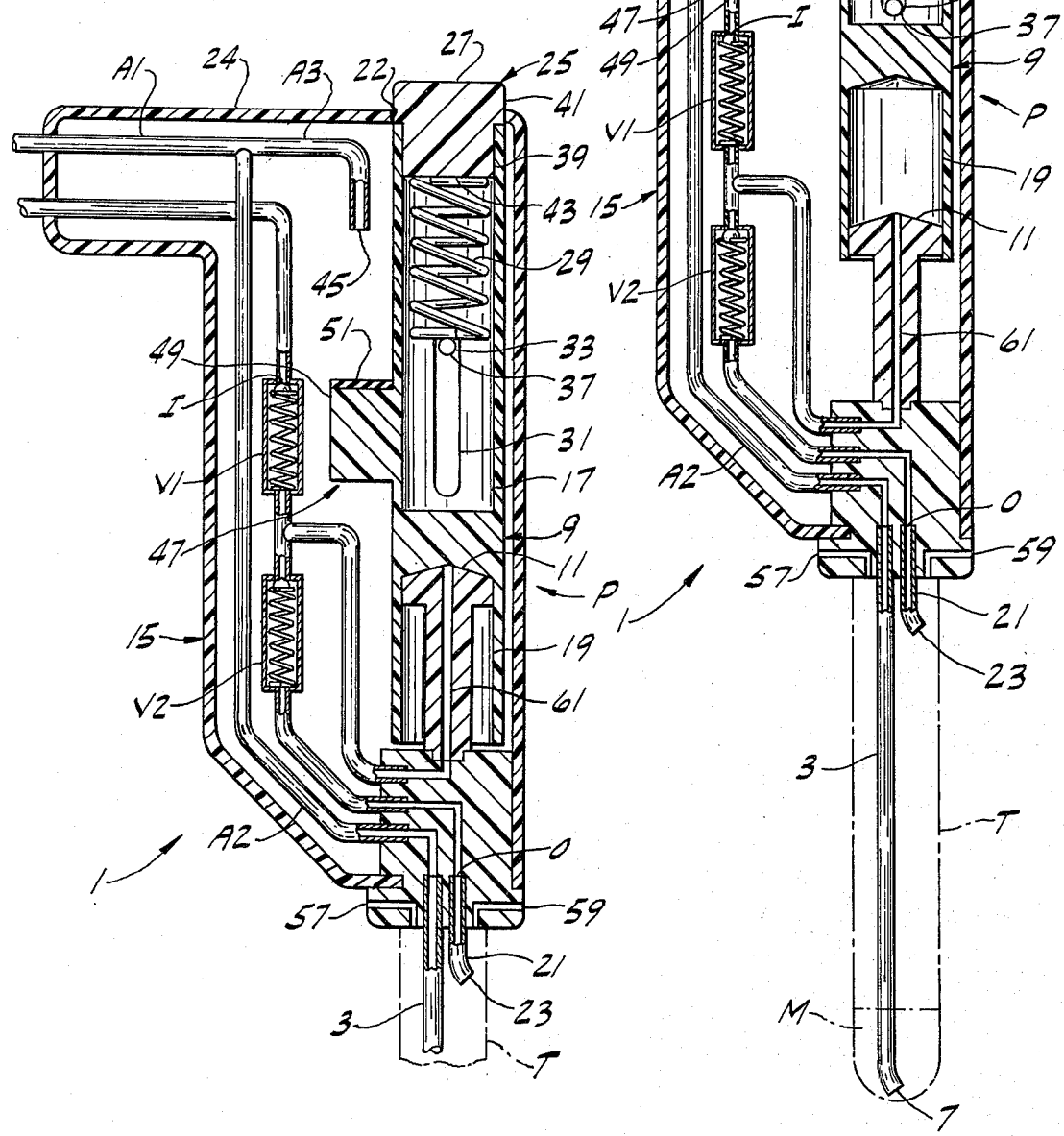
FIG. 3 is a sectional view of the test tube cleaner of FIG. 2 taken along line 3—3, showing the pump portion thereof in an initial or raised position.
FIG. 3A is a view similar to that of FIG. 3 showing a portion of the cleaner with the pump in a depressed position.

Referring now to the drawings, apparatus of the present invention for washing or cleaning contaminated laboratory containers such as test tubes, flasks and the like is indicated generally at 1 and is useful in radioimmunoassay testing or as a cleaner for test tubes and other laboratory containers. This apparatus or test tube cleaner 1 has a tube 3, one end 5 of which is connected to a source of negative pressure (e.g., a vacuum pump) and the other end 7 of which is inserted into a contaminated container, for example a test tube T. It will be understood that the containers with which cleaner 1 is used may have different sizes and shapes. Tube 3 has a length sufficient to reach the bottom of the container to remove by aspiration (i.e., suction) material M in the container.

A pump, generally indicated at P (see FIG. 3) has an inlet I and an outlet O and comprises a cylinder 9 for holding a quantity of washing material and a piston 11 slidable within the cylinder. The pump is connected to a source of washing material (not shown) and, when actuated, delivers washing material into the container. For this purpose, piston 11 is fixed while cylinder 9 is movable by a manual actuator 13 for discharging washing material from outlet O of pump P into container T. In response to actuation of pump P, aspiration of material in container T is interrupted during delivery of washing material. This is done by venting tube 3 to the atmosphere as is described hereinafter. Washing material thus delivered to container T and contaminants are withdrawn by aspiration from the container after pump P is deactuated. Tube 3 and pump P of cleaner 1 are mounted in a frame 15 designed to be held with one hand and readily portable.

As shown in FIG. 3, cylinder 9 is divided into an upper chamber 17 and a lower chamber 19, the quantity of washing material held by cylinder 9 being contained in the lower chamber. Further, pump P includes a first ball check valve V1 which opens during the intake portion of a pump cycle to admit washing material from the source into the pump and a second ball check valve V2 which opens during the delivery portion of a pump cycle to discharge washing material from the pump for delivery to container T. A second tube 21 has one end connected to pump outlet O and the other end 23 of the tube is inserted into container T for delivery of washing material from pump P to the container through tube 21.

The upper end of cylinder 9 projects through an opening 22 in the top surface 24 of frame 15 and manual actuator 13 includes a pushbutton 25 secured to the upper end of the cylinder and depressible from an initial position (shown in FIG. 3) when manual force is applied to top surface 27 of the pushbutton to a depressed position (shown in FIG. 3A). A spring 29 biases pushbutton 25 toward its initial position and the force of the spring returns the pushbutton to its initial position when manual force is removed from it. Two opposed longitudinal guide slots 31 are formed in the wall of cylinder 9 at the upper chamber level of the cylinder and one of these slots is shown in FIG. 3. A hole 33 is formed in each side wall 35 of frame 15 adjacent the lower end of each slot 31. A pin 37 is inserted through holes 33 and diametrically across chamber 17 through opposed slots 31 and acts as a seat for spring 29 which is sized to fit into upper chamber 17 of cylinder 9. Pushbutton 25 has a lower cylindrical section 39 whose diameter corresponds to the inside diameter of cylinder 9 and an upper cylindrical section 41 whose diameter corresponds to the outside diameter of the cylinder. Pushbutton 25 serves as a cap or plug for the upper end of cylinder 9 and when fitted into place the bottom surface 43 of pushbutton 25 contacts the upper end of spring 29.

Tube 3 has a port 45 vented to the atmosphere to stop aspiration of material M in container T. As shown in FIG. 3, tube 3 is preferably tee-shaped with one arm A1 including end 5 of tube 3, a second arm A2 including end 7 of the tube and a third arm A3 having an open end which constitutes port 45. A closure or seal for the port or vent, generally indicated at 47, includes a shoulder 49 extending from the outer wall of cylinder 9 (the movable portion of pump P) and a pad 51 of resilient material such as rubber affixed to the upper surface of the shoulder to serve as a seat to seal port 45. When pushbutton 25 is at its initial or raised position (FIG. 3) shoulder 49 is at its uppermost position and closure 47 seals port 45 of tube 3. When pushbutton 25 is depressed, closure 47 is moved away from port 45 (FIG. 3A) and it is vented or open to the atmosphere. Thus port 45 and closure 47 constitute means for venting the tube to stop aspiration.

In operation, laboratory containers, such as test tube T, to be cleaned are placed in racks or other suitable holders so that the mouth of each container is accessible. When the containers are being used in radioimmunoassay tests, the following described operation is performed after an incubation period and before radioactivity counting. End 5 of tube 3 is connected to a vacuum pump or other suitable source of negative pressure with the end 53 of a tube 55 connected to a source of washing material. It will be understood that a vacuum trap (not shown) is preferably located between the source of negative pressure and end 5 of tube 3 to collect contaminated material aspirated from a container T through the tube. The other end of tube 55 is connected to inlet I of pump P. After the appropriate connections are made, the user grips frame 15 with either hand and using his thumb presses down on pushbutton 25 and then releases it. This primes pump P with an initial charge or volume of washing material which is contained within chamber 19 of cylinder 9.

The user now inserts end 7 of tube 3, which serves as a suction probe, and end 23 of tube 21 into the mouth of a container by lowering cleaner 1 over the container mouth. When end 7 of tube 3 comes into contact with the contaminant material M in the container, aspiration of material through tube 3 to the vacuum trap or other suitable waste receptacle starts immediately. No other operation is required of the user to cause the initial aspiration to occur and it continues until the user decides to stop it. Two air passages, 57 and 59 respectively, open into container T when cleaner 1 is positioned over its mouth for air flow into the container so that aspiration occurs even though the container mouth is in peripheral contact with the body of cleaner 1. At this time, pushbutton 25 is in its initial position (FIG. 3) and port 45 of tube 3 is closed off by pad 51 of closure 47.

When the user wishes to deliver washing material to the container, he depresses pushbutton 25 with his thumb. The movement of pushbutton 25 away from its initial position produces a corresponding movement of cylinder 9 and closure 47 moves away from port 45 to uncover it so that it is vented to the atmosphere. Aspiration of material through tube 3 immediately ceases. Simultaneously, the washing material in chamber 19 of cylinder 9 is forced from the chamber through a passageway 61 to check valve V2 which opens to allow the washing material to flow out of pump P and through tube 21 for delivery to container T. This movement of cylinder 9 is the delivery portion of the pump cycle. End 23 of tube 21 is curved so that washing material discharged from the tube is directed at the side wall of the container to gently deliver the washing material into the container and to wash away any material adhering to the side wall.

After washing material is discharged into container T, the user releases the pressure on pushbutton 25 and it returns to its initial position under the force of spring 29. This produces a corresponding movement of cylinder 9 which is the intake portion of the pump cycle so that a new predetermined quantity or charge of washing material is drawn from the source, through tube 55 to inlet I of pump P and valve VI opens to admit the material into chamber 19 through passageway 61. When the pushbutton reaches its initial or rest position, pad 51 again seats against port 45 of tube 3 closing off the port. Aspiration of material in container T immediately starts with the material being drawn off through tube 3 as before.

By simply pressing and releasing pushbutton 25, the above steps may be repeated as many times as necessary to insure that all the contaminant material in container T is removed and that it is clean. When this is accomplished, the user then has only to raise the cleaner away from the mouth of the container T far enough for end 7 and end 23 of tubes 3 and 21, respectively, to clear the mouth of the container and he may then proceed to the next container to be cleaned. If the container just washed is being used in a radioimmunoassay test, it may now be removed to an area where the radioactivity of the solid phase material remaining in the tube is measured.

From the foregoing, it will be clear that aspiration of material from container T and delivery of washing solution to the container is controlled by a single pushbutton 25 and the person operating the cleaning apparatus 1 needs only one hand for the job. It will be understood that closure pad 51 is, in effect, a valve seat which keeps port 45 closed when pushbutton 25 is at its initial position but open at all other times. Further, the amount of washing material taken in by pump P and discharged into container T during each pump cycle may be a precisely metered amount which is obtained, for example, by fully depressing pushbutton 25 each time washing material is discharged. Alternatively, a score line may be marked around the circumference of the pushbutton at a predetermined point and the pushbutton only depressed as far as the score line or a mechanical stop may be provided. Also at no time during a cleaning operation does the material aspirated from the container T come into contact with the user of cleaner 1 and the contaminated material is therefore safely removed from the laboratory container without possibility of harm to the user.

It will also be understood that the cleaner 1 may be motorized so that pump P need not be manually actuated.

Referring now to FIG. 4, a second embodiment of the present invention is indicated generally at 1A in which aspiration of material M from container T is also interrupted during discharge of washing material. However, in this apparatus of FIG. 4, a tube 3A is blocked to interrupt aspiration rather than venting it to the atmosphere as is done with regard to the previously described embodiment. As before, end 5 of tube 3A is connected to a vacuum pump or other source of negative pressure and end 7 of the tube is inserted into container T. Also, end 53A of a tube 55A is connected to a supply of washing material and end 23 of tube 21 is inserted into container T. Pump P differs from that previously described in that a cylinder 9A is now fixed while a piston 11A is actuable by manual actuator 13. These components are installed in a frame 15A which has a guide bar 63 with an arcuate guide channel C in a front face 65 thereof. The curvature of channel C generally corresponds to that of the exterior of laboratory containers T to aid in positioning the container T relative to ends 7 and 23 of tubes 3A and 21. Further, a spring 29A of manual actuator 13 is disposed in cylinder 9A and seated against a wall 67 of the cylinder. The spring is in contact with forward wall 69 of piston 11A to bias a pushbutton 25A toward its initial position.

A stem 71 extends outwardly from rear wall 73 of piston 11A and frame 15A has an opening 75 in its rear wall 76 to accommodate the stem. In this embodiment, tube 3A has a resilient portion, generally designated F, and the tube is blocked by pinching off this portion. For this purpose, stem 71 has a transverse bore 77 through which passes resilient portion F of tube 3A and a longitudinal bore 79 extending from transverse bore 77 to the free end 81 of the stem. Pushbutton 25A has an extension 83 sized for insertion into longitudinal bore 79 and slidable therein for pinching engagement with tube 3A. A spring 85 is carried on extension 83 and seats against free end 81 of stem 71 to bias pushbutton 25A and extension 83 away from engagement with tube 3A.

In operation, the appropriate connections of tubes 3A and 55A are made and the user grasps frame 15A of cleaner 1A with either hand. He then primes pump P to admit an initial quantity of washing solution into cylinder 9A. Next, ends 7 and 23 of tubes 3A and 21, respectively, are inserted into the mouth of container T, channel C of guide bar 63 being used for this purpose. As before, aspiration of material M from container T begins as soon as end 7 of tube 3A comes into contact with the material. When washing material is to be delivered to the container, the user depresses pushbutton 25A with his thumb. This produces an initial movement of pushbutton 25A against the force of spring 85 and brings the tip of extension 83 into contact with the resilient portion of tube 3A and pinches it closed. This immediately interrupts aspiration of material from the container. Continuing pressure on pushbutton 25A moves piston 11A in cylinder 9A against the force of spring 29A. As shown in FIG. 4, resilient portion F of tube 3A is wrapped around stem 71 to provide play for the tube as the piston slides in the cylinder. The washing material in cylinder 9A flows through a check valve V2A and tube 21 for delivery into the container.

When the user releases his thumb from pushbutton 25A, spring 85 forces extension 83 away from contact with tube 3A, unblocking the tube and again allowing aspiration of material from the container. The force of spring 29A against piston 11A simultaneously returns pushbutton 25A to its initial position. Thus, in this embodiment, aspiration recommences as soon as the force on pushbutton 25A is released, whereas in the previous embodiment aspiration did not occur until the pushbutton returned to its initial position. The return of pushbutton 25A to its initial position corresponds to the intake portion of the pump cycle, as before, and a new quantity of washing material is taken into cylinder 9A through tube 55A and a valve V1A for the next delivery operation. After container T is clean, the user removes the container from apparatus 1A, readying it for the next container to be cleaned.

As before, the above described steps may be performed in washing laboratory containers used in radioimmunoassay testing after an incubation period and before radioactivity is measured.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for washing contaminated laboratory containers such as test tubes, flasks and the like comprising:
   a tube, one end of which is connected to a source of negative pressure and the other end of which is inserted into a contaminated container and having a length sufficient to reach the bottom thereof thereby to remove by aspiration created by said source of negative pressure material in the container;
   a pump connected to a source of washing material and to said container and which, when actuated, delivers washing material from said sources into the container; and
   means responsive to actuation of said pump to interrupt said aspiration during delivery of washing material, said washing material thus delivered to the container and contaminants being withdrawn by aspiration from the container after the pump is deactuated.

2. Apparatus as set forth in claim 1 further including means for manually actuating the pump.

3. Apparatus as set forth in claim 2 wherein the pump has an inlet and an outlet and comprises a cylinder for holding a quantity of washing material and a piston slidable within the cylinder, one of which is fixed and the other of which is movable by said actuation means for discharging washing material from the pump outlet into the container.

4. Apparatus as set forth in claim 3 wherein the actuation means includes a pushbutton connected to the movable portion of the pump and depressible from an initial position when manual force is applied thereto and a spring biasing the pushbutton towards its initial position, the force of the spring returning the pushbutton to its initial position when the manual force is removed and the movement of the pushbutton producing a corresponding movement of the movable portion of the pump.

5. Apparatus as set forth in claim 4 wherein the aspiration interruption means includes means for venting the tube to the atmosphere to stop aspiration of material in the container.

6. Apparatus as set forth in claim 5 wherein the venting means includes a port for the tube and means carried by the movable portion of the pump for closing the port when the pushbutton is in its initial position, the port being open to the atmosphere when the pushbutton is depressed.

7. Apparatus as set forth in claim 6 wherein the tube is tee-shaped with one arm of the tee including the first said end of the tube, a second arm of the tee including the other end of the tube, and a thrid arm of the tee having an open end engageable by the closing means, said open end constituting the port.

8. Apparatus as set forth in claim 6 wherein the movable portion of the pump is the cylinder which has a shoulder extending from the outer wall thereof with the closing means affixed to the shoulder.

9. Apparatus as set forth in claim 4 wherein the aspiration interruption means includes means for blocking the tube to stop aspiration of material in the container.

10. Apparatus as set forth in claim 9 wherein a portion of the tube is resilient.

11. Apparatus as set forth in claim 10 wherein the blocking means includes means for pinching off the resilient portion of the tube.

12. Apparatus as set forth in claim 11 wherein the movable portion of the pump has a stem extending outwardly therefrom with a transverse bore through which passes the resilient portion of the tube and a longitudinal bore extending from the transverse bore to the free end of the stem and the tube blocking means includes an extension of the pushbutton sized for insertion into the longitudinal bore of the stem and slidable therein for pinching engagement with the tube when manual force is applied to the pushbutton to pinch off the tube and block aspiration of material in the container.

13. Apparatus as set forth in claim 3 wherein the inlet to the pump includes a first check valve which opens during the intake portion of a pump cycle to admit washing material from the source into the pump and the outlet includes a second check valve which opens during the delivery portion of a pump cycle to discharge washing material from the pump for delivery to the container.

14. Apparatus as set forth in claim 13 further including a second tube one end of which is connected to the outlet of the pump and the other end of which is adapted for insertion into the container for delivery of washing material from the pump to the container through said second tube.

15. Apparatus as set forth in claim 14 wherein the other end of the second tube is curved so as to direct washing material delivered through said second tube at the side of the container thereby to wash away material adhering thereto.

16. Apparatus as set forth in claim 15 further including a third tube one end of which is adapted for connection to the source of washing material and the other end of which is connected to the inlet of the pump.

17. Apparatus as set forth in claim 1 further including a frame adapted to be handheld and in which the tube, pump and aspiration interruption means are mounted.

18. Apparatus as set forth in claim 17 wherein the frame further comprises a guide bar having a channel therein to aid in inserting the tube into the container.

* * * * *